United States Patent [19]

Temin

[11] 4,197,234

[45] Apr. 8, 1980

[54] DENTAL RESTORATIVE COMPOSITE COMPOSITIONS AND FILLER THEREFOR

[75] Inventor: Samuel C. Temin, Needham, Mass.

[73] Assignee: Colgate-Palmolive Company, New York, N.Y.

[21] Appl. No.: 923,901

[22] Filed: Jul. 12, 1978

[51] Int. Cl.$^2$ ........................... C08K 3/36; C08K 5/02
[52] U.S. Cl. ............................... 260/42.27; 260/42.53; 260/998.11
[58] Field of Search ............... 260/900, 998.11, 42.27, 260/42.53

[56] References Cited

U.S. PATENT DOCUMENTS 3,997,504  12/1976  Plymale ............................. 260/42.27

FOREIGN PATENT DOCUMENTS 2408640  9/1974  Fed. Rep. of Germany ........... 260/900

Primary Examiner—Sandra M. Person
Attorney, Agent, or Firm—Norman Blumenkopf; Herbert S. Sylvester; Murray M. Grill

[57] ABSTRACT

Polyfluorocarbon resin or polychlorofluorocarbon resin, especially polytetrafluoroethylene in powder form is added to a conventional inert inorganic finely divided filler for dental restorative composite compositions, in combination with conventional liquid polymerizable binder systems to provide a composite composition possessing improved mechanical properties, especially wear or abrasion resistance. As little as 1.0% by weight or less of the total weight of filler of the polyfluorocarbon or polychlorofluorocarbon resin powder imparts improved wear. Abrasion superior to conventional amalgams suitable for use on occlusal surfaces resistance is achieved.

5 Claims, No Drawings

DENTAL RESTORATIVE COMPOSITE COMPOSITIONS AND FILLER THEREFOR

BACKGROUND OF THE INVENTION

1. Field of the Invention

This invention relates to dental restorative composite compositions, and particularly, to the use of polyfluorocarbon resins or polychlorofluorocarbon resins, as a minor component of the finely divided, inorganic filler in dental restorative composite compositions.

2. Discussion of the Prior Art

Dental restorative composites, generally in the form of highly filled blends of a liquid polymerizable organic resin matrix and finely divided, inorganic particulate filler, have achieved wide commercial success and are used extensively in clinical dental practice. Basically, most of the dental restorative composites which have become commercially available, or which are described in the literature, are based upon the development of the system first disclosed by Bowen in U.S. Pat. No. 3,066,112. In the direct filling system or restorative composite described in this patent, the liquid polymerizable organic resin matrix or binder is principally the reaction product of bisphenol and glycidyl methacrylate, referred to as BIS-GMA, preferably combined with one or more other active monomers, referred to as reactive diluents, especially other dimethacrylates, for example, triethylene glycidyl methacrylate. The system also includes a catalyst or polymerization initiator, such as, for example, benzoyl peroxide. Preferably, to allow the polymerization to take place in a reasonable period of time, a polymerization accelerator or activator, such as, for example, N,N-dimethyl-p-toluidine is also present in the composite. A particularly attractive catalyst/accelerator combination, which eliminates the color-forming amine, is cumene hydroperoxide-acetyl thiourea which is disclosed in U.S. Pat. No. 3,991,008. Other ingredients, such as stabilizers or UV-absorbers may also be present in association with the polymerizable constituents to increase shelf life and otherwise prevent degradation of the properties of the restorative composite composition. Another ingredient usually used in dental restorative composite compositions is a coupling or fixing agent for enhancing the adhesion of the inert inorganic filler particles with the binder matrix. Ethylenically unsaturated organosilane compounds are generally used for this purpose. Still further, restorative composite compositions may include various dyes or pigments to obtain various shades to conform to the color of the tooth structure with which the restorative composite material is being used.

The composite restorative materials are generally provided for commercial use as multi-package systems, most typically a two package system, such as that described in U.S. Pat. No. 3,926,906 to Lee, et al. In these systems, the reactive monomers are generally provided in the form of a paste blended with the finely divided inert inorganic filler with the reactive diluent and/or catalyst and/or activator maintained separately from each other and/or from the polymerization ingredients or reactive diluent.

The most commonly used inorganic filler materials are typically crystalline quartz or amorphous silica, although other materials, such as, for example, fused silica, crystalline silica, glass beads, fused alumina and the like have also been disclosed. It has also been suggested to utilize fillers having a negative coefficient of thermal expansion such as, for example, betaeucryptite, a lithium aluminum silicate. The use of fillers of low negative coefficients of thermal expansion is highly desirable in order to more closely match the resultant composite with the tooth structure in terms of thermal expansion. Still further, there have been several proposals for utilizing radio-opaque glasses as a component of the filler in dental restorative composite compositions. The use of radio-opaque additives enables the cured composite to be distinguished from the surrounding tooth structure during x-ray analysis commonly used in dental diagnostics.

While many advances have been made in the mechanical properties of dental restorative composite compositions, there does not seem to have been sufficient consideration given to the wear or abrasion resistance characteristics of the cured dental composites and there is still area for improvement in this particular property. The tooth-matching composite restoratives, as described above, are now widely used for interior restorations and repair of incisor fractures. In fact, their use for restorations where aesthetics is important has grown to an almost complete replacement of the previously used amalgams. However, composite restorations have been found in clinical studies to be unsuitable for occlusion surface restorations because of poor wear manifested by loss of anatomical form. Studies by Leinfelder, et al., J. Prosthet. Dent., 33, 407–416 (1975); Williams, et al., Int. Assoc. Dent. Res., Abst. No. 560, March 1972 and Phillips, et al., J. Prosthet. Dent., 30, 891–897 (1973) have shown that previously known dental composite resins have insufficient resistance to abrasive wear to be used in class I and II cavity preparations. Because of the poor clinical performance of composite resins compared to amalgams, the American Dental Association at present does not condone their use for occlusal surfaces. Thus, there is a great incentive to devise or produce a dental composite resin with resistance to wear abrasion that is equal to or superior to amalgams.

It has been suggested in U.S. Pat. No. 3,469,317 to Jarby that polyethylene, polymonochlorotrifluoroethylene or polytetrafluoroethylene, as well as several other synthetic polymers, in finely divided form, can be used directly as temporary or permanent tooth fillings or as a cavity lining for permanent fillings, and that such fillings exhibit a high resistance to abrasion and chewing pressure. Nevertheless, it has not been suggested that the finely divided polyhalocarbons, i.e. halogen-substituted polyethylenes, could be added, as only a minor amount of the total inorganic finely divided filler component of dental restorative composite compositions, and still impart such large improvement in abrasion resistance.

OBJECTS AND SUMMARY OF INVENTION

It is accordingly an objective of the present invention to provide a dental restorative composite composition formed from a blend of liquid polymerizable resin binder matrix and a finely divided solid inert inorganic filler which has improved wear resistance, without loss of any other essential physical properties, such as compressive strength. It is also an object of the present invention to provide such dental restorative composite composition which can be used for occlusal surface restorations. These and other objects of the present invention will become more apparent from the following detailed description.

It has now been found that dental restorative composite compositions employing small percentages of polytetrafluoroethylene or other similar low friction coefficient non-toxic polyfluorocarbon resins or polychlorofluorocarbon resins, with other conventional fillers, impart to the cured composite greatly increased wear or abrasion resistance, without degrading the other desirable characteristics of the composite, such as coefficient of thermal expansion, translucency, thermal conductivity and compressive strangth.

The other components of the improved dental restorative composite compositions of this invention, such as polymerizable organic binder matrix, catalysts, accelerators, coupling agents, UV-absorbers, stabilizers, pigments and the like, can be selected from any of the type conventionally used in dental restorative composite compositions.

DETAILED DESCRIPTION AND PREFERRED EMBODIMENTS

Any of the non-toxic polyfluorocarbon resins or polyfluorochlorocarbon resins which are solid at room temperature and which exhibit the low coefficient of friction which characterize this class of fluorinated hydrocarbon polymers in general and polytetrafluoroethylene in particular can be used in this invention. Examples of the polyfluorocarbon resins include polytetrafluoroethylene, fluorinated ethylenepropylene copolymer (copolymer of tetrafluoroethylene and hexafluoropropylene), polyhexafluoropropylene, polyvinylidene fluoride ($-CH_2CF_2-$)$_n$, etc. Copolymers of tetrafluoroethylene and perfluoroalkyl vinyl ethers, such as DuPont's Teflon PFA, can also be used. Examples of the polyfluorochlorocarbon resins include, for example, polychlorotrifluoroethylene, etc. Generally, any of the resins obtained by polymerizing monomers of the lower alkenes such as ethylene, propylene, butene, and 4-methylpentene-1, in which all of the hydrogen atoms are replaced with fluorine and/or chlorine atoms, providing at least two-thirds of the halogens are fluorine, can be used as the wear resistance imparting additive in this invention. Fluorinated graphite, $(CF)_n$ can also be used. Polytetrafluoroethylene is the preferred additive.

The polyfluorocarbon or polyfluorochlorocarbon resin filler additive constitutes from about 1 to 10%, preferably about 1 to 5%, more preferably about 1.5 to 3%, of the total amount of filler. Generally, the total filler, including the additive, constitutes from at least about 50 parts by weight and up to about 90 parts by weight of the total filler and binder, and preferably, from about 65 parts by weight to about 85 parts by weight per 100 parts by weight of the total filler and binder and correspondingly, from 10 to 50 parts by weight, preferably 15 to 35 parts by weight of the polymerizable binder, per 100 parts by weight of the filler and binder.

Any of the conventional fillers can constitute the major proportion of the total weight of filler. Representative of such suitable filler materials include, for example, silica, glass beads, aluminum oxide, fused silica, fused or crystalline quartz, lithium aluminum silicate, barium glass, and the like.

The particle sizes of filler materials, including the conventional filler and the polyhalocarbon additive, generally range from submicron to about 125 microns, with the average particles having an average mean diameter in the range of from submicron to about 30 microns and preferably, from about 2 to 5 microns for the conventional filler and from submicron to about 30 microns for the polyhalocarbon additive, most preferably about 0.1 to 5 microns.

A preferred filler contains about 95 to 99 parts by weight of the amorphous silica and about 1 to 5 parts by weight of polytetrafluoroethylene per 100 parts by weight of filler particles.

The dental restorative composite composition of this invention therefor includes, per 100 parts by weight, about 50 to 90 parts by weight, preferably 65 to 85 parts by weight of finely divided inert inorganic filler particles (including conventional siliceous filler plus polyhalocarbon additive), about 10 to 50 parts by weight, preferably about 15 to 35 parts by weight of liquid polymerizable organic resin binder (including polymerizable monomers and other reactive monomers or diluents), about 0.1 to 2% by weight based on the weight of the binder of catalysts, about 0.1 to 2% by weight based on the weight of binder of accelerators, and about 0 to 5% by weight based on the weight of the binder, preferably about 1 to 5% by weight of organosilane coupling agent.

The polymerizable organic resin binder can generally be any acrylic resin, such as, for example, methylmethacrylate, methylacrylate, ethylmethacrylate, etc., although dimethacrylates such as those derived from aliphatic glycols or those having structures known in the art as vinyl esters, are more suitable. The preferred polymerizable monomers are those based upon BIS-GMA and other di-, tri- and tetra-methacrylates, such as disclosed by Bowen in the aforementioned U.S. Pat. No. 3,066,112. Other suitable polymerizable monomer systems which can be used in this invention are disclosed, for example, in U.S. Pat. Nos. 3,179,623; 3,539,533; 3,730,947; 3,766,132; 3,774,305; 3,835,090; 3,839,065; 3,854,009; 3,860,556; 3,862,920; 3,882,600; 3,911,581; 3,923,280; and 3,991,008. Each of these patents teach suitable polymerizable monomers, reactive diluents, catalysts, accelerators and other conventionally used adjuvants and additives in dental restorative composite compositions for such applications as dental fillings, dental cements and the like. Accordingly, the disclosures of these references should therefor be considered to be incorporated herein by reference. For example, the polymerization catalyst is generally a peroxide such as benzoyl peroxide, 2,-4-dichlorobenzoyl peroxide, 4-chlorobenzoyl peroxide, etc. Suitable activators or accelerators which cause decomposition of the catalyst to provide free radicals for promoting the polymerization reaction include such preferred compounds as N,N-dialkylanilines and N,N-dialkyltoluidines. A particularly desirable class of catalysts, based on their greater shelf stability, are hydroperoxides which are used in conjuction with substituted thioureas as accelerators, as disclosed in U.S. Pat. No. 3,991,008. Other suitable activators include, for example, paratoluenesulfinic acid, para-tolyldiethanol amine and other tertiary amines. The binder system can also include various well kn' wn stabilizers or UV-absorbers to increase the shelf life of the unpolymerized composite resin compositions.

It is also preferred to include coupling agents for enhancing the adhesion between the polymerizable resin binder and the filler. Examples of suitable coupling agents, include, for example, vinyltrichlorosilane, tris(2-methoxyethoxy) silane, tris(acetoxy) vinylsilane, 1-N-(vinylbenzylaminoethyl)aminopropyltrimethoxy silane -3, 3-methacryloxypropyltrimethoxy silane, etc. Generally, the filler particles are treated with the silane coupling agent prior to blending the filler and liquid polymerizable matrix or it can be added to the polymerizable resin binder prior to addition of the inorganic particulate filler.

The dental restorative composite composition can be prepared, for example, by mixing each of the ingredients in any conventional manner, although a preferred packaging system is that disclosed, for example, in U.S. Pat. No. 3,926,906 to Lee, Jr., et al. According to the so-called two package system described in this patent, each package contains the unpolymerized monomers and any reactive diluents and inorganic filler and additive, preferably in the proportion present in the final product. One package contains the initiator or catalyst and the other package contains the reductant or accelerator. By combining roughly equal portions from the two packages, the catalyst and accelerator in each package react with each other to generate free radicals, thereby causing polymerization of the polymerizable resin system.

The composite resin composition can also be blended, prior to curing, with pigments or dyestuffs in amounts required to more closely approximate, in the cured composite material, the natural color of the tooth enamel, with which the composite material is being used. Examples of suitable pigments or dyestuffs include, for example, iron oxide black, cadmium yellow, cadmium orange, fluorescent zinc oxides, titanium dioxide, etc.

The following non-limiting illustrative examples will further demonstrate the practice of this invention.

EXAMPLE 1

Dental restorative composites were prepared by first blending (a) 25% by weight of an organic binder containing a 1:1 by weight mixture of bis-phenol A-glycidyl methacrylate product (BIS-GMA)-hexamethylenedimethacrylate mixture containing 5% by weight, based on the total monomers, of silane coupling agent (3-methacryloxypropyl trimethoxysilane) and 1% by weight, based on the total monomers, of acetylthiourea reductant; and (b) 75% by weight of filler. In Sample No. 1, the filler was 100% IMSIL A-10 (amorphous silica having an average particle size of about 2 microns), and in Run No. 2, the filler consisted of 98% by weight of the silica and 2% by weight of Teflon powder of submicron mean average particle size. The resultant pastes were treated with cumene hydroperoxide in an amount of about 2% by weight based on the total monomers, and cured in cups or molds. The composite resin was cured in about 3 minutes at room temperature. The cured composites were tested for their wear or abrasion characteristics on a sliding wear machine, in comparison with a commercial amalgam.

The sliding wear test machine permits measurement of the depth of the wear track with time caused by a stylus of human enamel pressed against a rotating disc of the material tested. The pressure of the stylus and the speed of rotation are equivalent to the stress and strain occurring in human mastication. The apparatus is fully described in the 1977 PhD thesis, "Wear and Degradation of Polymers and Polymeric Composite Materials", submitted to the University of Connecticut by Paresh J. Sheth and is available from that school. This machine has been found to rank material with respect to wear in the same order as found by clinical studies. Commercial dental restorative composites were found to be markedly inferior to amalgams in wear abrasion against human enamel in results obtained with this sliding wear tester.

The wear data was summarized and compared with a commercial amalgam (Velvaloy, a product of S. S. White & Company) in the following table.

TABLE I

| WEAR OR EXPERIMENTAL COMPOSITES | | |
|---|---|---|
| Sample | Time to reach to 50 microns depth (hrs) | Wear depth after 50 hrs. (microns) |
| Amalgam | 90 | 17.5 |
| 1. IMSIL A-10 | 43 | 60 |
| 2. IMSIL A-10 + Teflon | 150 (est.)* | 5 |

*The time to reach 50 microns depth is only estimated in this table since with the composite containing Teflon, the wear test was terminated at 120 hours, when the wear depth was only about 38 microns.

It is therefore seen from the above table, that addition of the Teflon powder to a silica filled composite which wears much more rapidly than conventional amalgam results in a filled composite that has greater wear or abrasion resistance than amalgam.

What is claimed is:

1. In a dental restorative composition having improved resistance to abrasion comprising from about 50 to 90 parts by weight of finely divided filler particles, and about 10 to about 50 parts by weight of liquid polymerizable organic resin binder, the improvement wherein about 1% to about 10% by weight of the filler is selected from the group consisting of polyfluorocarbon resin and polyfluorochlorocarbon resin.

2. The dental restorative composite composition of claim 1 which includes from 65 to 85 parts by weight of finely divided inorganic filler and 35 to 15 parts by weight of the liquid polymerizable organic resin binder.

3. The dental restorative composition of claim 1 wherein said resin is polytetrafluoroethylene.

4. A dental restorative composition of claim 1 wherein the resin comprises from about 1% to about 5% by weight of the filler.

5. The dental restorative composition of claim 1 wherein said total filler comprises 95 to 99% by weight of amorphous silica and 1 to 5% by weight of polytetrafluoroethylene.

* * * * *